United States Patent [19]

Toth et al.

[11] Patent Number: 4,598,080
[45] Date of Patent: Jul. 1, 1986

[54] CERTAIN-2-METHYL-6-{4-[1-PHENYL-1-HYDROXYPROPYL]-PHENOXYMETHYL} PYRIDINES WHICH INHIBIT MICROSONAL MONOXYGENASE SYSTEMS IN LIVER

[75] Inventors: Edit Toth; Jozsef Törley; Eva Palosi; Szabolcs Szebereneyi; László Szporny; Sandor Görög; Istvan Hajdu, all of Budapest, Hungary

[73] Assignee: Richter Gedeon Vegyeszeti Gyar Rt, Budapest, Hungary

[21] Appl. No.: 565,831

[22] Filed: Dec. 27, 1983

[30] Foreign Application Priority Data

Dec. 28, 1982 [HU] Hungary ................................. 4183

[51] Int. Cl.⁴ ..................... C07D 213/30; A61K 31/44
[52] U.S. Cl. ..................................... 514/277; 546/344; 546/339
[58] Field of Search ................. 546/339, 344; 424/263; 514/277

[56] References Cited

U.S. PATENT DOCUMENTS 4,094,908 6/1978 Toth et al. ........................ 564/324

OTHER PUBLICATIONS

Burger, Medicinal Chemistry, Second Edition, p. 497, Interscience Pub. (1960).
Roberts et al., Basic Principles of Organic Chemistry, pp. 351, 353, 386, 417, 418, 421, 906, Benjamin Publishers (1965).
Chem. Abstracts, vol. 22, p. 410, article 1.
Chem. Abstracts, vol. 35, 1871(2).
Chem. Abstracts, vol. 40, 4712(5).
Chem. Abstracts, vol. 42, 1015(b).
Chem. Abstracts, vol. 47, 9548(e).
Chem. Abstracts, vol. 50, 12390(c).
Chem. Abstracts, vol. 50, 2509(i).
Chem. Abstracts, vol. 55, 17915(e).
Chem. Abstracts, vol. 55, 15413(b).
Chem. Abstracts, vol. 75, P 103682(b).
Chem. Abstracts, vol. 76, P 11 9921(k).
Chem. Abstracts, vol. 82, 16477(q).
Chem. Abstracts, vol. 90, 86062(q).
Chem. Abstracts, vol. 92, 52 927(b).
Organisch-Chemische Arzneimittel und Ihre Synonyma, Martin Negwer, p. 960, Akademie-Verlag-Berlin, 1978.

*Primary Examiner*—Alan L. Rotman
*Attorney, Agent, or Firm*—Karl F. Ross; Herbert Dubno

[57] ABSTRACT

The invention relates to new pyridine derivatives of the formula (I)

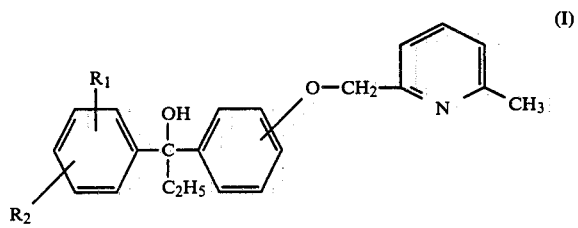

wherein
$R_1$ and $R_2$ independently represent hydrogen, halogen, trihalomethyl, alkyl having from one to 4 carbon atoms or alkoxy having from one to 4 carbon atoms, and acid addition and quaternary ammonium salts thereof.

According to another aspect of the invention there are provided processes for the preparation of these compounds.

The compounds of the formula (I) are pharmacologically active. In particular, they inhibit the microsomal monooxigenase enzyme system of the liver. Pharmaceutical compositions containing them as active ingredient are also within the scope of the invention.

4 Claims, No Drawings

CERTAIN-2-METHYL-6-{4-[1-PHENYL-1-HYDROXYPROPYL]-PHENOXYMETHYL}PYRIDINES WHICH INHIBIT MICROSONAL MONOXYGENASE SYSTEMS IN LIVER

This invention relates to new pyridine derivatives and acid addition and quaternary salts thereof. More particularly, the invention concerns new pyridine derivatives of the formula (I)

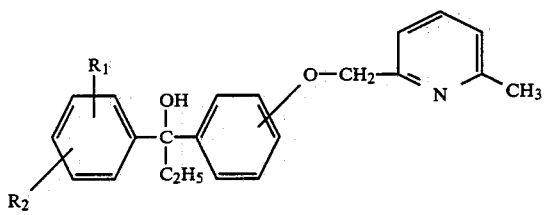

wherein $R_1$ and $R_2$ independently represent hydrogen, halogen, trihalomethyl, alkyl having from one to 4 carbon atoms or alkoxy having from one to 4 carbon atoms, and acid addition and quaternary salts thereof. The invention further relates to a process for the preparation of these compounds and pharmaceutical compositions containing them as active ingredient.

The term "halogen" as used herein embraces all of the halogens, and may be fluorine, chlorine, bromine or iodine, preferably fluorine or chlorine.

The term "alkyl having from one to 4 carbon atoms" refers to straight or branched chain aliphatic hydrocarbon groups containing from one to 4 carbon atoms.

The term "alkoxy having from one to 4 carbon atoms" is used herein to refer to straight or branched chain alkoxy groups containing from one to 4 carbon atoms.

The trihalomethyl groups may contain any of the halogens listed above.

The acid addition salts and quaternary salts of these compounds are also within the scope of the invention.

Compounds of analogous structure are disclosed for example in the following references: C.A. 22, 410[1]; 35, 1871[2]; 40, 4712[5]; 42, P 1015 b; 47, 9548 e; 50, 12390 c; 50, 2509 i; 55, 17915 e; 55, 15413 b; 75, P 103682 b; 76, P 119921 k; 82, 16477 g; 90, 86082 g; 92, 52927 b. None of these citations does, however, mention any pharmaceutical activity of the disclosed compounds.

According to a further aspect of the present invention there is provided a process for the preparation of the compounds of the formula (I), wherein $R_1$ and $R_2$ have the same meaning as defined above, and salts thereof, which process comprises (a) reacting a propiophenone of the formula (II)

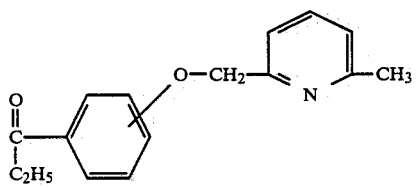

with an organometallic compound of the formula (III)

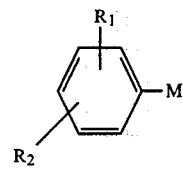

wherein $R_1$ and $R_2$ are as defined above, and

M is an alkali metal, preferably lithium, sodium, potassium, or an MgX group, in which X is halogen; or (b) reacting a compound of the formula (IV)

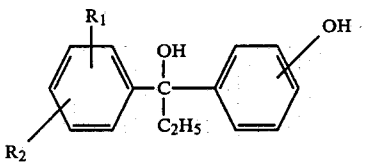

wherein $R_1$ and $R_2$ are as defined above, preferably in the form of an alkali metal or quaternary ammonium phenolate thereof, with a compound of the formula (V)

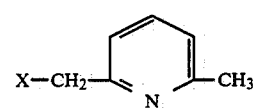

wherein X is halogen, or a salt thereof, preferably in the presence of an acid binding agent; or (c) reacting a propiophenone of the formula (VI)

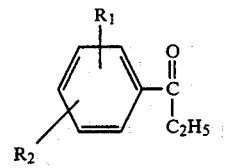

wherein $R_1$ and $R_2$ are as defined above, with a Grignard reactant of the formula (VII)

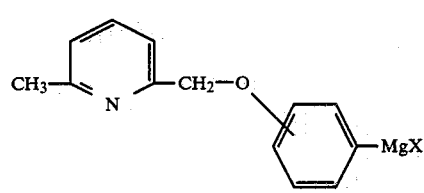

wherein

X is halogen, and if desired, converting any of the products obtained by process variants (a) to (c) into their acid addition or quaternary ammonium salts, or converting a product obtained as an acid addition salt into a corresponding base and/or converting a free base into an acid addition or quaternary ammonium salt thereof.

According to a preferred embodiment of process variant (a) a propiophenone of the formula (II) is reacted with an organometallic compound of the formula (III), preferably with a suitably substituted phenyl magnesium chloride or bromide or a suitably substituted phenyl lithium in a dry inert organic solvent. The reaction is preferably carried out in an aprotic organic solvent, e.g. in an aliphatic ether such as diethyl ether, di-n-butyl ether or diethylene glycol dimethyl ether, an alicyclic ether such as tetrahydrofurane, dioxane, an aliphatic or aromatic hydrocarbon such as ligroin, benzene, toluene, xylene, dimethyl sulfoxide or hexamethyl phosphorus amide, or a mixture of these solvents. The organometallic compound is used in an at least equimolar amount. The reaction is preferably performed in an inert gas atmosphere, e.g. in nitrogen or argon. The reaction temperature may range from $-60°$ C. up to the boiling point of the solvent, and preferably is between $-30°$ C. and $100°$ C. When the reaction is complete, the reaction mixture is decomposed, preferably with an aqueous ammonium chloride solution, and the obtained compound of the formula (I) is separated. The product can be purified by known techniques, e.g. by distillation or crystallization.

According to process variant (b) a compound of the formula (IV), preferably in the form of its alkali metal or quaternary ammonium phenolate, is condensed with a tertiary amine of the formula (V). As a tertiary amine for example diethylaminoalkyl mesylate, tosylate, bromide or preferably chloride is employed, as a free base or a salt, e.g. hydrogen halide thereof. The reaction is preferably carried out in an inert organic solvent, in the presence of an acid binding agent, under anhydrous conditions or in a mixture of water and an organic solvent. As organic solvents for example esters such as ethyl acetate, ethers such as dioxane, tetrahydrofurane or diethyl ether, hydrocarbons such as ligroin, benzene, toluene or xylene, halogenated hydrocarbons such as chloroform, chlorobenzene, acid amides such as dimethyl formamide, ketones such as acetone, methyl ethyl ketone or methyl isobutyl ketone, alcohols such as ethanol, propanol, etc. are employed. Compounds of the formula (IV) can be converted into their phenolates by methods known in the art, e.g. with alkali metal alcoholates, amides, hydrides, hydroxides, carbonates or quaternary ammonium compounds. Preferred acid binding agents include inorganic and tertiary organic bases, e.g. sodium hydroxide, potassium hydroxide, potassium carbonate, triethyl amine, pyridine, etc. The reaction is optionally performed in the presence of a catalyst. As a catalyst for example alkali metal halides, preferably alkali metal iodides may be used. The reaction temperature may be varied within a wide range, and preferably is between $20°$ C. and the boiling point of the solvent.

According to process variant (c) the Grignard compounds of the formula (VII), in which X preferably represents a bromine atom, are preferably reacted with an equimolar amount of the propiophenones of formula (VI), in a dry inert organic solvent, similarly to process variant (a).

If desired, the compounds of the formula (I) can be converted into their acid addition salts or quaternary ammonium salts by methods well known in the art. The acid addition salts can be prepared by means of inorganic or organic acids, e.g. hydrogen halides such as hydrochloric acid, hydrogen bromide, etc., sulfuric acid, phosphoric acids, formic acid, acetic acid, propionic acid, oxalic acid, glycolic acid, maleic acid, fumaric acid, tartaric acid, succinic acid, ascorbic acid, citric acid, malic acid, salicylic acid, lactic acid, benzoic acid, cinnamic acid, asparaginic acid, glutaminic acid, N-acetyl-asparaginic acid, N-acetyl-glutaminic acid, alkylsulfonic acids, such as methanesulfonic acid, arylsulfonic acids such as p-toluene-sulfonic acid, etc. According to a preferred embodiment the corresponding acid is added to a solution of a compound of the formula (I) in an inert solvent, e.g. ethanol, and the salt formed is precipitated, preferably with a water-immiscible organic solvent such as diethyl ether. Quaternization is preferably carried out with a lower alkyl, alkenyl or benzyl halide or alkyl sulfate. The reaction is performed in an organic solvent, preferably acetone, acetonitrile, ethanol or in a mixture thereof, at a temperature between room temperature and the boiling point of the solvent. The quaternary salts can be isolated e.g. by filtration and if desired, are purified by crystallization.

The starting compounds are known or can be prepared by methods known in the art. The ketones of the formulae (II) and (VI) can for example be synthesized by the Friedel-Crafts type ketone synthesis (G. A. Olah: Friedel-Crafts and related reactions, III/1, Ed.: Interscience Publishers 1964, pp. 1–63).

The compounds of the formulae (III) and (VII) are for example prepared from the corresponding aryl halides by known techniques (M. S. Kharash et al.: Grignard reactions of nonmetallic substances, Ed.: Prentice-Hall. Inc. (1954) pp. 5–90), while the alkali metal-organic compounds can be prepared following the method disclosed in Houben-Weyl: Methoden der Organischen Chemie, XIII/1, pp. 134–159 and 389–405 (1970).

The compounds of the formula (VI) can for example be synthesized from the corresponding propiophenones by reaction with the corresponding Grignard-reactants (see e.g. M. S. Kharash et al.: Grignard reactions of nonmetallic substances, Ed.: Prentice-Hall Inc. (1954) pp. 134–143).

The compounds of the formula (I) provided by the invention are pharmacologically active. In particular, they inhibit the microsomal monooxygenase enzyme system of liver, and can therefore be used in therapy to inhibit or reduce the toxic effect of exogenic xenobiotic substances, which are transformed into toxic, active metabolites in the liver (D. M. Jerina et al.: Science, 185, 573 (1974)), resulting in liver necrosis, blood discrasia, carcinosis. In pharmaceutical combinations the compounds according to the invention may increase the duration of the effect of other active ingredients.

The enzyme inhibiting activity of the new compounds was tested in vivo, by measuring the change of hexobarbital oxidase activity. Female Hann.-Wistar rats, each weighing 50 to 60 g. were treated orally with a single 40 mg./kg. dose of the test compound. 1 and 24 hours after the administration of the active ingredient, the animals were narcotized with a 60 mg./kg. i.v. dosage of hexobarbital sodium, and the time elapsed until complete wakening was measured (Noordhoek, J.: Eur. J. Pharmacol., 3, 242 (1968)). The data were recorded, and the mean values, the standard errors, as well as the percentage increase with respect to the controls were calculated for each group. As a reference compound Proadifen ((2-diethylaminoethyl)-$\alpha,\alpha$-diphenyl valerate), i.e. the most effective known compound, was employed, in a dose of 100 mg./kg. The hexobarbital concentration of the plasm, measured on the instant wakening, was the same for both the treated and the control animals, and thus the increase of narcosis period was not due to a certain central nervous interaction (Jori, A. et al.: Biochem. Pharmacol., 19, 2687 (1970)). The results are shown in Table 1.

Abbreviations:

$\bar{x}$ = mean value

S.E. = standard error of the mean value n = number of animals

The control group was treated with a placebo.

A = 2-methyl-6-{4-[1-(4-chlorophenyl)-1-hydroxypropyl]-phenoxymethyl}-pyridine

B = 2-methyl-6-{4-[1-(2,5-dimethylphenyl)-1-hydroxypropyl]-phenoxymethyl}-pyridine

TABLE 1

| Compound | Hexobarbital 1 hour | Narcosis period in % of the control | n |
|---|---|---|---|
| A | 259 ± 11.4 | 155 ± 9.6 | 10 |
| B | 135 ± 6.7 | 174 ± 7.2 | 10 |
| Proadiphene (100 mg/kg) | 241 ± 9.6 | 44 ± 5.7 | 10 |
| Control* | 100 ± 8.9(1) | 100 ± 10.8(2) | 10 |

*Control 100% = 41.3 ± 3.67 ($\bar{x}$ ± S.E./min.(1))
48.12 ± 5.19 ($\bar{x}$ ± S.E./min.(2))

Both the increase of the narcosis period and the permanence of the effect (the compounds being effective even 24 hours after administration) indicate that the compounds of formula (I) inhibit the biotransformation of xenobiotic agents in the liver for a long time. The effect of the new compounds provided by the invention is better than that of Proadiphene also from qualitative aspects, since, in contrast to Proadiphene, the initial inhibiting effect caused by the compounds according to the invention is not followed by an increase, i.e. induction, of the activity of the microsomal enzyme system.

The enzyme inhibiting activity of the compounds of the formula (I) was further tested by determining the activity of the polysubstrate monooxygense enzyme system of the liver after treatment with the placebo and the compounds according to the invention, respectively. Female H.Wistar rats weighing 50 to 60 g. each were administered a single 40 mg./kg. dose of the test compounds, orally. Two hours after treatment the animals were decapitated and the livers were eliminated. After rinsing with a physiological saline solution at 0° C., drying and weighing, the livers were homogenized in a 0.1 molar Tris-HCl buffer (pH = 7.2), containing 1.15% of potassium chloride at 0° C., centrifuged at 9000 g for 20 minutes, and the supernatant (postmitochondrial fraction) was used for further investigations. The microsomal fraction was prepared following the method developed by Cinti D. L. et al.: Biochem. Pharmacol., 21, 3249 (1972). The activity of aniline hydroxylase was determined from the velocity of p-aminophenol formation according to Chabra R. S. et al.: Toxicol. Appl. Pharmacol., 22, 50 (1972). The activity of the aminopyrine demethylase was measured from the amount of the formaldehyde formed, according to Gourlay G. K. et al.: Biochem. Pharmacol., 27, 965 (1978). The control groups were treated with a placebo. The results are shown in Table 2, in % of the control.

TABLE 2

| Compound | Aniline hydroxylase (nmoles/g/min) | Aminopyrine demethylase (nmoles/g/min) |
|---|---|---|
| Control | 100 ± 2.7 | 100 ± 4.2 |
| A | 66 ± 8.0 | 55 ± 4.4 |

TABLE 2-continued

| Compound | Aniline hydroxylase (nmoles/g/min) | Aminopyrine demethylase (nmoles/g/min) |
|---|---|---|
| B | 77 ± 7.5 | 63 ± 4.4 |

Control ($\bar{x}$ ± S.E.) = 19.8 ± 0.53 nmoles/g/min
260.7 ± 11.2 nmoles/g/min

As appears from the data of Table 2, the compounds according to the invention substantially inhibit the activity of the biotransforming enzyme system already two hours after administration.

The central nervous activities of the compounds according to the invention were examined on mice and rats with the following methods: electroshock (Swinyard, E. A., Brown, W. C., Goodman, L. S.: J. Pharmacol. Exp. Ther. 106, 319 (1952)), metrazole spasm (Everett, G. M., Richards, R. K.: J. Pharmacol. Exp. Ther. 81, 402 (1944)), thiosemicarbazide spasm (Da Venzo, J. P., Greig, M. E., Cormin, M. A.: Amer. J. Physiol. 201, 833 (1961)), strychnine spasm (Kerley, T. L., Richards, A. G., Begley, R. W., Abreu, B. B., Wesver, L. C.: J. Pharmacol. Exp. Ther. 132, 360 (1961)), nicotine spasm (Stone, C. A., Mecklenburg, K. L., Torhans, M. L.: Srch. Int. Pharmacodyn. 117, 419 (1958)), rotarod test (Kinnard, W. C., Carr, C. J.: J. Pharmacol. Expt. Ther. 121, 254 (1957)), physostigmine lethality preventing effect (Nose, T., Kojima, M.: Europ. J. Pharmacol. 10, 83 (1970)), yohimbine potentiation effect (Quinton, R. M..: Brit. J. Pharmacol. 21, 51 (1963)), and analgesic activity (Bianchi, G., Franceschini, J..: Brit. J. Pharm. Chemother. 9, 280 (1954)).

The compounds of the formula (I) when tested by the above methods proved completely ineffective, whereas Proadiphene exerted an anticonvulsive side effect (H. Ippen: Index Pharmacorum (1970), 40S 3.1).

The acute toxicity of the compounds of the formula (I) was tested on H-Wistar rats of both sexes, weighing 160 to 180 g. each. The compounds were administered in a single 500 mg./kg. dose, orally. The animals were observed for 14 days. The results are set forth in Table 3.

TABLE 3

| Compound (500 mg./kg. p.o.) | Perished animals (%) | n |
|---|---|---|
| A | 0 | 10 |
| B | 0 | 10 |
| Proadiphene | 90 | 10 |

As appears from the data of Table 3, the toxicity of the instant compounds is considerably lower than that of Proadiphene, accordingly their therapeutic index is much more favorable.

The pharmacologically active compounds according to the invention can be used in therapy in the form of pharmaceutical compositions, which are formulated as preparations suitable for oral, rectal and/or parenteral administration. For oral administration tablets, dragees or capsules are prepared. The oral formulations contain as a vehicle e.g. lactose or starch, as an excipient or a granulation aid e.g. gelatine, carboxymethyl cellulose sodium, methyl cellulose, polyvinyl pyrrolidone or starch gum, as a disintegrating substance e.g. potato starch or microcrystalline cellulose, ultraamylopectine or formaldehyde casein, etc. The formulations may also contain adhesives and lubricants such as talc, colloidal silica, stearin, calcium or magnesium stearate, etc.

Tablets are prepared for example by wet granulation and subsequent pressing. A mixture of the active ingredient and the vehicle and optionally a part of the disintegrating agent are granulated with an aqueous, alcoholic or aqueous-alcoholic solution of the excipients in a suitable equipment, and the granulate is dried. The remaining portion of the disintegrating substance, lubricant, anti-adhesive or optional further additives is then added to the granules, and the mixture is pressed to tablets. If desired, the tablets are prepared with a dividing line, which facilitates administration. Tablets can be prepared also from a mixture of the active ingredient and suitable additives by direct pressing.

If desired, the tablets can be converted into gragees, using protecting, flavouring agents and pigments generally known for the preparation of pharmaceutical compositions, e.g. sugar, cellulose derivatives (methyl or ethyl cellulose, carboxymethyl cellulose sodium, etc.), polyvinylpyrrolidone, calcium phosphate, calcium carbonate, food pigments, food oil varnishes, aroma substances, iron oxide pigments, etc.

Capsules are prepared by filling a mixture of the active ingredients and additives into suitable capsules.

For rectal administration the compositions are formulated as suppositories, which contain in addition to the active ingredient a carrier mass, called adeps pro suppository. Suitable carriers include vegetable fats, e.g. hardened vegetable oils, triglycerides of fatty acids having 12 to 18 carbon atoms, preferably Witepsol (a registered trade mark). The active ingredient is homogenously distributed in the melted carrier mass, and suppositories are prepared by casting.

For parenteral administration injectable preparations are prepared. To prepare an injectable solution the active ingredient is dissolved in distilled water and/or various organic solvents, e.g. glycol ethers, optionally in the presence of dissolution aids, e.g. polyoxyethylene sorbitane monolaurate, monooleate or monostearate (Tween 20, Tween 60, Tween 80). The injectable solutions may contain also various additives, e.g. preserving agents, such as benzyl alcohol, p-oxy-benzoic acid methyl or propyl ester, benalkonium chloride or phenyl mercuri borate, etc., antioxidants such as ascorbic acid, tocopherol, sodium pyrosulfate and optionally complexing agents to bind metal traces such as ethylene diamine tetraacetate, buffers to adjust the pH and optionally local anaesthetics such as lidocaine. The injectable solutions are filtered, filled into ampoules and sterilized. The daily dose, depending on the state of the patient, varies between 1.0 and 200.0 mg./kg., preferably 2.0 and 40.0 mg./kg, which is preferably administered in several smaller dose units.

The invention will be further illustrated by the following Examples but it is not intended to limit the scope of the invention to the Examples.

EXAMPLE 1

2-Methyl-6-{4-[1-(2-trifluoromethylphenyl)-1-hydroxypropyl]-phenoxymethyl}-pyridine To 200 ml. of a 0.5 molar, ethereal 2-trifluoromethylphenyl-lithium solution a solution of 12.7 g of 4-[(6-methyl-pyrid-2-yl)-methoxy]propiophenone in 290 ml. of dry ether is added dropwise, with stirring under argon atmosphere, at −20° C., and the reaction mixture is stirred for three further hours. It is then decomposed with a saturated, aqueous ammonium chloride solution, the aqueous phase is extracted with ether, the ethereal phase is washed to neutral with water, dried over anhydrous magnesium sulfate, and evaporated in vacuo. The crude product is crystallized from a mixture of hexane and ethyl acetate. 8.2 g. of the title compound are obtained, melting at 128° to 129° C.

Analysis for $C_{23}H_{22}F_3NO_2$: Calculated: C: 68.81%, H: 5.52%, F: 14.20%, N: 3.49%; Found: C: 68.66%, H: 5.61%, F: 14.32%, N: 3.76%.

EXAMPLE 2

2-Methyl-6-{4-[1-(4-fluorophenyl)-1-hydroxypropyl]-phenoxymethyl}-pyridine

To a Gringard reactant prepared from 2.2 g. of magnesium turnings and 25 g. of 4-[(6-methylpyrid-2-yl)-methoxy]-bromobenzene in 120 ml. of dry tetrahydrofurane a solution of 9.1 g. of 4-fluoropropiophenone in 45 ml. of tetrahydrofurane is added dropwise at 0° C. The reaction mixture is stirred at room temperature for two additional hours, and is then decomposed with a saturated aqueous ammonium chloride solution, under cooling. The aqueous phase is extracted with tetrahydrofurane. The tetrahydrofurane phase is washed with a saturated sodium chloride solution, dried over anhydrous magnesium sulfate, and evaporated in vacuo. Crystallization of the crude product from a mixture of ethyl acetate and n-hexane yields 15.2 g. of the title compound, melting at 103° to 104° C.

Analysis for $C_{22}H_{22}FNO_2$: Calculated: C 75.19%, H 6.31%, F 5.40%, N 3.99%; Found: C 75.00%, H 6.33%, F 5.58%, N 4.20%.

EXAMPLE 3

2-Methyl-6-{4-[1-(4-chlorophenyl)-1-hydroxypropyl]-phenoxymethyl}-pyridine 13.1 g. of α-ethyl-α-(4-chlorophenyl)-4-hydroxybenzyl-alcohol, 14 g. of anhydrous potassium carbonate, 0.85 g. of tetrabutylammonium hydrogensulfate and 7.8 g. of 2-methyl-6-chloromethyl-pyridine in 140 ml. of ethyl acetate are boiled for 18 hours. The solvent is distilled off under reduced pressure, to the residue water is added, and it is extracted with ether. The ethereal solution is washed to neutral with a 5% aqueous potassium hydroxide solution and subsequently water, dried over anhydrous magnesium sulfate, and evaporated in vacuo. Crystallization of the residue from a mixture of hexane and ethyl acetate yields 13.6 g. of the title compound, melting at 100° to 101° C.

Analysis for $C_{22}H_{22}ClNO_2$: Calculated: C: 71.83%, H: 6.03%, Cl: 9.64%, N: 3.81%; Found: C: 71.75%, H: 6.25%, Cl: 9.80%, N: 3.66%.

A solution of the base in dry acetone is treated with hydrochloric acid in either under cooling, and the precipitated crystalline hydrochloride is filtered off and dried. Melting point: 124.5° to 125.5° C.

To a solution of the base in dry acetone a solution of methanesulfonic acid in dry ether is added under cooling. The precipitated crystalline methanesulfonate is filtered off and dried. Melting point: 126.5° to 127.5° C.

EXAMPLE 4

2-Methyl-6-{4-[1-(2,5-dimethylphenyl)-1-hydroxypropyl]-phenoxymethyl}-pyridine

To a Grignard reactant prepared from 1.5 g. of magnesium turnings and 11.1 g. of 2-bromo-p-xylene in 33 ml. of dry tetrahydrofurane 12.7 g. of 4-[(6-methylpyrid-2-yl)-methoxy]-propiophenone in 30 ml. of dry tetrahydrofurane are added dropwise, under slight reflux. The reaction mixture is slightly boiled for an additional 30 minutes, and is then poured onto a saturated aqueous solution of ammonium chloride. The aqueous phase is extracted with tetrahydrofurane, the tetrahydrofurane phases are combined, and washed with a saturated sodium chloride solution. After drying over anhydrous magnesium sulfate, the solvent phase is evaporated under reduced pressure. Crystallization of the residue from a mixture of n-hexane and ethyl acetate yields 13.4 g. of the title compound, melting at 91° to 92° C.

Analysis for $C_{24}H_{27}NO_2$: Calculated: C: 79.74%, H: 7.53%, N: 3.87%; Found: C: 79.87%, H: 7.71%, N: 4.10%.

The hydrochloride and methanesulfonate of the base are prepared essentially following the procedure described in Example 3.

Melting point of the hydrochloride: 115° to 116° C.
Melting point of the methanesulfonate: 116° to 118° C.

EXAMPLE 6

2-Methyl-6-{4-[1-(2-methoxyphenyl)-1-hydroxypropyl]-phenoxymethyl}-pyridine 7.8 g of α-ethyl-α-(2-methoxyphenyl)-4-hydroxybenzyl-alcohol are dissolved in 65 ml. of methylisobutyl ketone, 9.1 g. of anhydrous potassium carbonate are added, and the reaction mixture is brought up to a boil. Thereafter, a solution of 4.7 g. of 2-methyl-6-chloromethyl-pyridine in 20 ml. of methylisobutyl ketone is added dropwise, and the reaction mixture is slightly boiled for 4 additional hours. After cooling, the reaction mixture is filtered off, and the filtrate is evaporated under reduced pressure. The residue is dissolved in benzene, the solution is washed with a 5% aqueous potassium hydroxide solution and then with water, dried over anhydrous magnesium sulfate and evaporated to dryness in vacuo. The crude product is crystallized from a mixture of ethyl acetate and cyclohexane. Melting point: 110° to 111° C.

Analysis for $C_{23}H_{25}NO_3$: Calculated: C: 76.00%, H: 6.93%, N: 3.85%; Found: C: 76.18%, H: 6.77%, N: 3.92%.

EXAMPLE 5

2-Methyl-6-{4-[1-(2,5-dimethylphenyl)-1-hydroxypropyl]-phenoxymethyl}-pyridine methoiodide 3.6 g. of the corresponding base are dissolved in 18 ml. of dry acetone, 1.2 ml. of methyl iodide are added, and the reaction mixture is slightly refluxed. After cooling the precipitated crystalline quaternary salt is filtered off, washed with diisopropyl ether and dried. 4.1 g. of the title compound are obtained, melting at 156° to 158° C.

8-Methyl-6-{4-81-(4-chlorophenyl)-1-hydroxypropyl]-phenoxymethyl}-pyridine methoiodide is prepared in an analogous way. Melting point: 107° to 108.5° C.

Similarly there can be prepared the following compounds by proper selection of the starting substances:
2-Methyl-6-{4-[1-(3-trifluoromethylphenyl)-1-hydroxypropyl]-phenoxymethyl}-pyridine
Melting point: 82° to 83° C.
Analysis for $C_{23}H_{22}F_3NO_2$:
Calculated: C: 68.81%, H: 5.52%, F: 14.20%, N: 3.49%; Found: C: 69.10%, H: 5.67%, F: 14.37%, N: 3.66%.

2-Methyl-6-{4-[1-(3-chlorophenyl)-1-hydroxypropyl]-phenoxymethyl}-pyridine
Melting point: 96° to 97° C.
Analysis for $C_{22}H_{22}ClNO_2$: Calculated: C: 71.83%, H: 6.03%, Cl: 9.64%, N: 3.81%; Found: C: 71.88%, H: 6.18%, Cl: 9.52%, N: 3.92%.

2-Methyl-6-{4-[1-(4-trifluoromethylphenyl)-1-hydroxypropyl]-phenoxymethyl}-pyridine
Melting point: 119° to 121° C.
Analysis for $C_{23}H_{22}F_3NO_2$:
Calculated: C: 68.81%, H: 5.52%, F: 14.20, N: 3.49%; Found: C: 68.73%, H: 5.50%, F: 14.11%, N: 3.40%.

2-Methyl-6-{2-[1-(2-methoxyphenyl)-1-hydroxypropyl]-phenoxymethyl}-pyridine
Melting point: 125° to 126° C.
Analysis for $C_{23}H_{25}NO_3$: Calculated: C: 76.00%, H: 6.93%, N: 3.85%; Found: C: 75.87%, H: 7.20%, N: 3.82%.

2-Methyl-6-{2-[1-(2,5-dimethylphenyl)-1-hydroxypropyl]-phenoxymethyl}-pyridine
Melting point: 114° to 115° C.
Analysis for $C_{24}H_{27}NO_2$ Calculated: C: 79.74%, H: 7.53%, N: 3.87%; Found: C: 79.71%, H: 7.44%, N: 3.81%.

EXAMPLE 7

The new compounds according to the invention can for example be converted into the following pharmaceutical compositions.

Tablets

Composition of a single tablet:

| | |
|---|---|
| active ingredient | 100.0 mg. |
| lactose | 184.0 mg. |
| potato starch | 80.0 mg. |
| polyvinyl pyrrolidone | 8.0 mg. |
| talc | 12.0 mg. |
| magnesium stearate | 2.0 mg. |
| aerosil (colloidal SiO2) | 2.0 mg. |
| ultraamylopectine | 12.0 mg. |

From the above ingredients 400-mg. tablets are prepared by wet granulation and subsequent pressing.

Active ingredient: 2-methyl-6-{4-[1-(4-chlorophenyl)-1-hydroxypropyl]-phenoxymethyl}-pyridine.

Dragées

Tablets as described above are coated with a coating prepared from sugar and talc in a known manner. Dragées are polished with a mixture of bee wax and carnouba wax. Weight of a dragée: 500.0 mg.

Suppositories

Composition of a suppository:

| | |
|---|---|
| active ingredient | 100.0 mg. |
| lactose | 200.0 mg. |
| basic substance (e.g. Witepsol H) | 1700.0 mg. |

The basic substance is melted and then cooled to 35° C. The active ingredient is thoroughly blended with the lactose, and the mixture is homogenized in the basic substance with a homogenizator. The obtained mass is poured into cool molds. One suppository weights 2000 mg. Active ingredient: 2-methyl-6-{4-[1-(4-chlorophenyl)-1-hydroxypropyl]-phenoxymethyl}-pyridine Capsules Composition of a single capsule:

| active ingredient | 50.0 mg. |
|---|---|
| lactose | 100.0 mg. |
| talc | 2.0 mg. |
| potato starch | 30.0 mg. |
| cellulose (microcrystalline) | 8.0 mg. |

The active ingredient is thoroughly admixed with the additives, the mixture is passed through a 0.32-mm. sieve, and filled into hard gelatine capsules No. 4.

Active ingredient: 2-methyl-6-{4-[1-(2,5-dimethylphenyl)-1-hydroxypropyl]-phenoxymethyl}-pyridine Suspension Composition of 100 ml. of suspension:

| active ingredient | 1.0 g. |
|---|---|
| sodium hydroxide | 0.26 g. |
| citric acid | 0.30 g. |
| nipagin (4-hydroxybenzoic acid methylester sodium salt) | 0.10 g. |
| Carbopol 940 (polyacrylic acid) | 0.30 g. |
| ethanol (96%) | 1.00 g. |
| raspberry aroma | 0.60 g. |
| sorbite (70% aqueous solution) | 71.00 g. |
| distilled water ad | 100.00 ml. |

To a solution of nipagin and citric acid in 20 ml. of distilled water Carbopol is added in small portions, with vigorous stirring, and the solution is allowed to stand for 10 to 12 hours. Thereafter a solution of the above amount of sodium hydroxide in 1 ml. of distilled water is added dropwise, followed by dropwise addition of an aqueous solution of sorbite and an ethanolic raspberry aroma solution, with stirring. Active ingredient is added in small portions, and the mixture is homogenized. The suspension is supplemented with distilled water ad 100 ml., and the suspension syrup is passed through a colloidal mill. Active ingredient: 2-methyl-6-{4-[1-(2,5-dimethylphenyl)-1-hydroxypropyl]-phenoxymethyl}-pyridine.

We claim:
1. A pyridine derivative

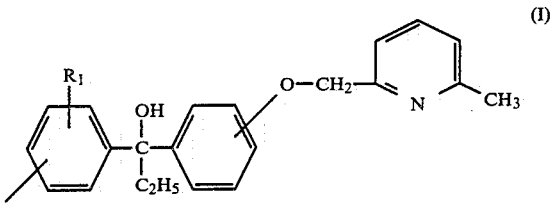

wherein
$R_1$ and $R_2$ independently represent hydrogen, halogen, trihalomethyl, alkyl having from one to 4 carbon atoms or alkoxy having from one to 4 carbon atoms,
or a pharmaceutically acceptable acid addition salt thereof.

2. A compound selected from the following group:
2-methyl-6-{4-[1-(2-trifluoromethylphenyl)-1-hydroxypropyl]-phenoxymethyl}-pyridine,
3-methyl-6-{4-[1-(4-fluorophenyl)-1-hydroxypropyl]-phenoxymethyl}-pyridine,
2-methyl-6-{4-[1-(4-chlorophenyl)-1-hydroxypropyl]-phenoxymethyl}-pyridine,
2-methyl-6-{4-[1-(2,5-dimethylphenyl)-1-hydroxypropyl]-phenoxymethyl}-pyridine,
2-methyl-6-{4-8  1-(2-methoxyphenyl)-1-hydroxypropyl]-phenoxymethyl}-pyridine,
2-methyl-6-{4-[1(3-trifluoromethylphenyl)-1-hydroxypropyl]-phenoxymethyl}-pyridine,
2-methyl-6-{4-[1-(3-chlorophenyl)-1-hydroxypropyl]-phenoxymethyl}-pyridine,
2-methyl-6-{4-[1-(4-trifluoromethylphenyl)-1-hydroxypropyl]-phenoxymethyl}-pyridine,
2-methyl-6-{2-[1-(2-methoxyphenyl)-1-hydroxypropyl]-phenoxymethyl}-pyridine and,
2-methyl-6-{2-[1-(2,5-dimethylphenyl)-1-hydroxypropyl]-phenoxymethyl}-pyridine or a pharmaceutically acceptable acid addition salt thereof.

3. A pharmaceutical composition for inhibiting the microsonal monooxygenase system in the liver containing a pharmaceutically effective amount of a compound of the formula (I) as claimed in claim 1, or a pharmaceutically acceptable acid addition salt thereof, together with a pharmaceutically acceptable carrier or auxiliary substance.

4. A method of inhibiting the microsonal monooxygenase system in the liver of a susceptible animal subject which comprises administering to the animal subject a pharmaceutically effective amount of a compound as defined in claim 1 or a pharmaceutically acceptable acid addition salt thereof.

* * * * *